United States Patent [19]

McClure

[11] Patent Number: 4,734,037

[45] Date of Patent: Mar. 29, 1988

[54] MESSAGE SCREEN

[76] Inventor: J. Patrick McClure, 372-E Bel Marin Keys Blvd., Novato, Calif. 94947

[21] Appl. No.: 832,464

[22] Filed: Feb. 21, 1986

[51] Int. Cl.⁴ .............................................. G09B 19/00
[52] U.S. Cl. ..................................... 434/236; 40/427; 434/307
[58] Field of Search .................. 434/236, 307; 40/427

[56] References Cited

U.S. PATENT DOCUMENTS

| | | | |
|---|---|---|---|
| 2,969,531 | 1/1961 | Stewart | 340/347 R |
| 3,014,724 | 12/1961 | Cryder et al. | 273/DIG. 28 X |
| 3,060,795 | 10/1962 | Becker | 434/236 X |
| 3,278,676 | 10/1966 | Becker | 434/236 X |
| 3,542,365 | 11/1970 | Gantz | 273/DIG. 28 X |
| 3,568,356 | 3/1971 | Berman | 273/DIG. 28 X |
| 3,728,480 | 4/1973 | Baer | 273/DIG. 28 X |

FOREIGN PATENT DOCUMENTS 1198344  6/1959  France ................................ 434/307

Primary Examiner—William H. Grieb
Attorney, Agent, or Firm—Fliesler, Dubb, Meyer & Lovejoy

[57] ABSTRACT

A transparent sheet is disclosed having a message thereon. The sheet has a first side adapted to be attached facing a plate which is normally viewed by a viewer and a second side facing the viewer. The message is arranged to be readably intelligible from the second side but is not liminally visible to the viewer when viewed from a normal viewing distance from the second side under normal viewing conditions. The message has a subliminal effect upon the viewer when viewed from the normal viewing distance from the second side under normal viewing conditions. A viewer can electively subject him or herself to subliminal messages while viewing television at leisure.

9 Claims, 1 Drawing Figure

U.S. Patent    Mar. 29, 1988    4,734,037
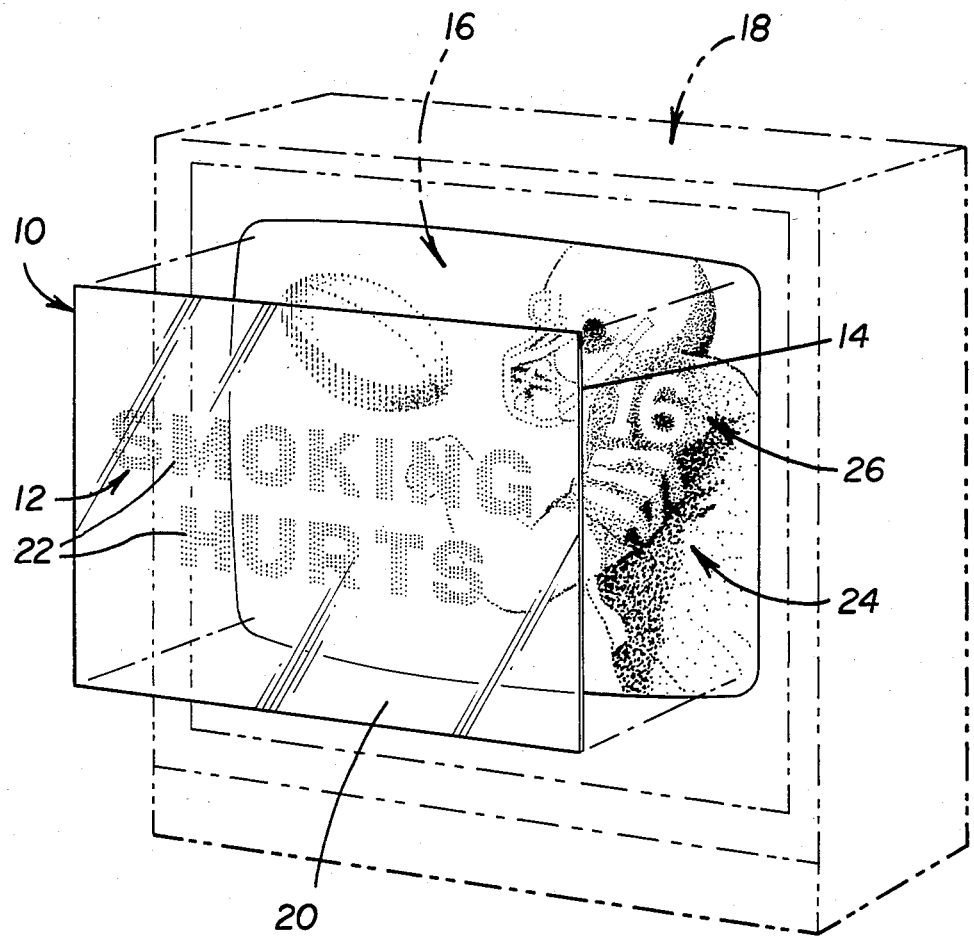

MESSAGE SCREEN

DESCRIPTION

1. Technical Field

The invention relates generally to an article of manufacture through which subliminal messages can be presented to a viewer while the viewer is looking at a television program, through a window, or the like.

2. Background Art

Various types of sheets or screens have been attached in front of the viewing screen of a television set for various purposes. For example, about the time of the advent of colored television sets thin plastic sheets were marketed which were attached in front of the screen of a black and white television set and which colored sky blue along their tops, green in their centers and brown at their bottoms, the idea being to simulate reception of television pictures in color.

Various overlay masks have been utilized for playing different games on television set screens. Such are set forth in, for example, U.S. Pat. No. 3,728,480 issued Apr. 17, 1973 to R. H. Baer, U.S. Pat. No. 3,568,356, issued Feb. 3, 1969 to M. R. Berman, U.S. Pat. No. 3,014,724, issued Dec. 26, 1961 to R. E. Cryder, et al and U.S. Pat. No. 3,542,365, issued Nov. 24, 1970 to E. J. Gantz.

The screens or sheets placed in front of the television set screen in each of the above patents either have no indicia on them whatsoever, or have indicia on them which can be readily seen by a viewer located in the normal television viewing position, for example, 6 to 12 feet from the front of the television set. Furthermore, none of the aforementioned patents are concerned with delivery of a subliminal message to the viewer.

The inclusion of subliminal messages with the signal sent to a television receiver is known. In such an instance, the subliminal messages are flashed onto the screen occassionally and for very short periods of time, the frequency of repetition and the period of time being selected so that viewer is unaware of the fact that the message is being flashed upon the screen. To carry this out, however, requires expensive equipment. Furthermore, the message is not under the control of the viewer.

The present invention is concerned with solving one or more of the problems set forth above.

DISCLOSURE OF INVENTION

In accordance with an embodiment of the present invention an article of manufacture is provided which comprises a transparent sheet having a message thereon, the sheet having a first side adapted to be attached facing a plate which is normally viewed by a viewer and a second side facing the viewer. The message is arranged to be readably intelligible from the second side. The message is not liminally visible to the viewer when viewed from a normal viewing distance from the second side under normal viewing conditions. The message has a subliminal effect upon the viewer when viewed from the normal distance from the second side under normal viewing conditions.

In accordance with another embodiment of the present invention a television set is set forth having a screen, a transparent sheet having a message thereon, the sheet having a first side attached to the screen, the sheet having a second side facing away from the screen and towards the position occupied by a viewer during use of the set. The message is arranged to be readably intelligible from the second side. The message is not liminally visible to the viewer when viewed from a normal viewing distance from the second side under normal viewing conditions. The message has a subliminal effect upon the viewer when viewed from the normal viewing distance from the second side under normal viewing conditions.

Another embodiment yet of the present invention is a method of subliminally delivering a message to a viewer. The method comprises attaching a first side of a transparent sheet facing a plate which is normally viewed by the viewer, with the first side facing the plate, the sheet having a second side facing the viewer. The sheet bears the message which is arranged to be readably intelligible from the second side. The message is not liminally visible to the viewer when viewed from a normal viewing distance from the second side under normal viewing conditions. The message has a subliminal effect upon the viewer when viewed from the normal viewing distance from the second side under the normal viewing conditions. An image is provided on the plate which is visible to the viewer through the sheet.

An article of manufacture in accordance with the present invention is inexpensive and allows a person to subliminally effect his or her behaviour. For example, the message might read eating is bad, hunger is good, smoking hurts, etc. Such a message can be delivered while the person is viewing television in a normal manner thus reinforcing good habits such as eating less, stopping smoking, or the like.

BRIEF DESCRIPTION OF DRAWING

The single FIGURE of the drawing shows an article of manufacture in accordance with the present invention in combination with a television set.

BEST MODE FOR CARRYING OUT INVENTION

The single FIGURE of the drawing illustrates a transparent sheet 10 having a message 12 thereon. The sheet 10 has a first side 14 which is adapted to be attached facing a plate 16 such as the screen of a common television receiver 18, either being attached directly to the picture tube or attached to a pane of clear glass or plastic which protects the picture tube. The sheet 10 also has a second side 20 which normally faces the viewer. The message is arranged to be readably intelligible from the second side 20. That is, the message properly reads from left to right if in English, right to left if in Hebrew, etc., if viewed from in front of the second side 20 of the sheet 10.

In the single FIGURE of the drawing the message 12 is shown as being formed from a plurality of dots 22. This is done to figuratively indicate that the message is not liminally visible to the viewer of the television set 18 when viewed from a normal viewing distance in front of the second side 20 of the sheet 10 under normal viewing conditions. Thus, when one is watching a television program 24 on a television set 18 which has the sheet 10 attached over the television screen 16, one is consciously and liminally aware of only the television program 24. However, message 12 still has a subliminal effect upon the viewer. Since most people watch several hours of television a day such a subliminal message can be highly effective in helping viewers to modify their behaviour.

While a plurality of dots 22 are shown as constituting the message 12 it is not anticipated that this is necessarily the way that the message may be made to be not liminally visible but still have a subliminal effect. In fact, if a plurality of dots 22 are utilized, such dots 22 will generally be of very low intensity so as to maintain the message 12 as being not liminally visible. More generally, the message 12 can be incorporated into the sheet 10 in any convenient manner. For example, if the sheet 10 is of a material such as glass the message 12 may be lightly etched on to the glass. Alternatively, the message 12 may be embossed on to a plastic sheet 10, lightly imprinted as solid letters on to the sheet 10, laser printed on to the sheet 10, laser etched on to the sheet, or the like.

In a particularly preferred embodiment of the present invention the message 12 is printed on to either the first side 14 or the second side 20 of the sheet 10 with a material which causes the message 12 to not be liminally visible but to have a subliminal effect as discussed above and which will fluoresce when exposed to ultraviolet light. In this manner, the user of the sheet 10 can check at any time to see that the message 12 is correctly worded.

In accordance with a preferred embodiment of the present invention the sheet 10 will simply attach directly to the screen 16 of the television set 18. Any of a number of soft limp transparent plastic films are sufficiently tacky to have the attribute of soft-adherence to the transparent front screen 16 of a television set 18. For example, the sheet 10 can be made of polyvinyl chloride having appropriate amounts of plasticizer so as to make the surfaces of the sheet 10 tacky.

It is also anticipated as being within the scope of the invention to utilize a rigid sheet 10 which may be held in place by use of a separate adhesive, by mounting to a suitable frame, or the like.

In accordance with the method of the present invention the sheet 10 is attached as discussed above and the television set 18 is turned on to provide an image 26 on the television screen 16 which is visible to the viewer through the sheet 10. The image 26 will generally be in the nature of a television image 26 of the usual sort.

It should be noted that while all of the above discussion relates to the use of the article of manufacture of the present invention in connection with a television screen, the invention is not so limited. That is, the article of manufacture of the present invention may also be attached in front of any cathode ray tube, for example a computer screen, or may be attached on a window through which the viewer regularly looks, for example, the front window of an automobile, or may otherwise be attached in any convenient place for viewing, for example, to a window which overlooks attractive scenary. In such instances it will generally be necessary that there be some type of a back lighting, i.e., some type of light source, natural or artificial, which provides light which shines through the transparent sheet 10 and towards the eyes of the viewer.

INDUSTRIAL APPLICABILITY

The article of manufacture of the present invention is particularly useful in combination with a conventional home television set 18. It provides a method for subliminally aiding the viewer in attaining a desired behaviour pattern.

While the invention has been described in connection with certain specific embodiments thereof it will be realized by those skilled in the art that there are various other advantages, objects and uses of the invention which fall within the scope of the invention as defined by the appended claims.

I claim:
1. An article of manufacture, comprising:
   a transparent sheet having a message thereon, said sheet having a first side adapted to be attached facing a plate which is normally viewed by a viewer and a second side facing said viewer, said message being arranged to be readably intelligible from said second side, said message being of a construction sufficient so that it is not liminally visible to said viewer when viewed from a normal viewing distance from said second side under normal viewing conditions but being of a construction sufficient to have a subliminal effect upon said viewer when viewed from said normal viewing distance from said second side under said normal viewing conditions.

2. An article of manufacture as set forth in claim 1, wherein said plate comprises a screen of a cathode ray tube.

3. An article of manufacture as set forth in claim 1, wherein said plate comprises a screen of a televison set.

4. An article of manufacture as set forth in claim 3, wherein said first side of said sheet adheres to said screen.

5. An article of manufacture as set forth in claim 1, wherein said message is of a construction such that it can be liminally viewed when illuminated by an ultraviolet light source.

6. A television set having a television screen, a transparent sheet having a message thereon, said sheet having a first side attached to said television screen, said sheet having a second side facing away from said television screen and towards a position occupied by a viewer during use of said set, said message being arranged to be readably intelligible from said second side, said message being of a construction sufficient to not be liminally visible to said viewer when viewed from a normal viewing distance from said second side under normal viewing conditions but being of a construction sufficient to have a subliminal effect upon said viewer when viewed from said normal viewing distance from said second side under said normal viewing conditions.

7. A television set as set forth in claim 6, wherein said message is of a construction such that it can be liminally viewed when illuminated by an ultraviolet light source.

8. A method of subliminally delivering a message to a viewer, comprising:
   attaching a first side of a transparent sheet, said sheet having a first side adapted to be attached facing a plate which is normally viewed by said viewer, with said first side facing said plate, said sheet having a second side facing said viewer, said sheet bearing said message, said message being arranged to be readably intelligible from said second side, said message being of a construction sufficient to not be liminally visible to said viewer when viewed from a normal viewing distance from said second side under normal viewing conditions but being of a constructtion sufficient to have a subliminal effect upon said viewer when viewed from said normal viewing distance from said second side under said normal viewing conditions; and
   providing an image on said plate which is visible to the viewer through said sheet.

9. A method as set forth in claim 8, wherein said plate is a television screen and said image is a television image.

* * * * *